(12) United States Patent
Weeber (10) Patent No.: US 8,382,281 B2
(45) Date of Patent: Feb. 26, 2013

(54) DIFFRACTIVE MULTIFOCAL LENS HAVING RADIALLY VARYING LIGHT DISTRIBUTION

(75) Inventor: Henk A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 13/006,521

(22) Filed: Jan. 14, 2011

(65) Prior Publication Data
US 2011/0109875 A1 May 12, 2011

Related U.S. Application Data

(62) Division of application No. 12/109,251, filed on Apr. 24, 2008, now Pat. No. 7,871,162.

(60) Provisional application No. 60/047,699, filed on Apr. 24, 2008.

(51) Int. Cl.
*G02C 7/02* (2006.01)

(52) U.S. Cl. ............ 351/159.11; 351/159.78; 359/558; 359/571

(58) Field of Classification Search .............. 351/177, 351/159.11, 159.01, 159.02, 159.05, 109.11, 351/109.15, 159.73, 159.74, 159.78; 359/558, 359/571

See application file for complete search history.

(56) References Cited

U.S. PATENT DOCUMENTS

| | | | |
|---|---|---|---|
| 3,367,734 A | 2/1968 | Bystricky et al. |
| 4,637,697 A | 1/1987 | Freeman |
| 4,642,112 A | 2/1987 | Freeman |
| 4,655,565 A | 4/1987 | Freeman |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,932,970 A | 6/1990 | Portney |
| 4,995,714 A | 2/1991 | Cohen |
| 4,995,715 A | 2/1991 | Cohen |
| 5,016,977 A | 5/1991 | Baude et al. |
| 5,056,908 A | 10/1991 | Cohen |
| 5,066,301 A | 11/1991 | Wiley |

(Continued)

FOREIGN PATENT DOCUMENTS

| | | |
|---|---|---|
| EP | 343067 A1 | 11/1989 |
| EP | 457553 A2 | 11/1991 |

(Continued)

OTHER PUBLICATIONS

International Search Report for Application No. PCT/IB2009/005590, mailed on Sep. 30, 2009, 3 pages.

(Continued)

*Primary Examiner* — Tuyen Tra
(74) *Attorney, Agent, or Firm* — AMO Groningen B.V.

(57) ABSTRACT

The present invention provides improved ophthalmic lenses and methods for their design and use. Monofocal and multifocal diffractive ophthalmic lenses having reduced light scatter and/or improved light energy distribution properties are provided. These properties are provided by the diffractive profiles of the invention, often having subtly shaped echelettes with appropriately curving profiles. Light scatter may be generated by the sharp corners associated with vertical steps between adjacent conventional diffractive echelettes. Smooth diffractive profiles of the invention reduce light scatter. Light energy directed towards non-viewing diffractive orders may have a unwanted effects on vision quality. Diffractive profiles of the invention may limit the light energy in certain, selected orders, thereby improving viewing quality and mitigating unwanted effects such as dysphotopsia. Diffractive profiles of the invention can also vary the light energy distributed between individual echelettes, providing additional advantages in various viewing situations.

13 Claims, 10 Drawing Sheets

U.S. PATENT DOCUMENTS

| | | |
|---|---|---|
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,144,483 A | 9/1992 | Cohen |
| 5,225,858 A | 7/1993 | Portney |
| 5,229,797 A | 7/1993 | Futhey et al. |
| 5,652,638 A | 7/1997 | Roffman et al. |
| 5,699,142 A | 12/1997 | Lee et al. |
| 5,748,282 A | 5/1998 | Freeman |
| 5,760,871 A | 6/1998 | Kosoburd et al. |
| 5,796,462 A | 8/1998 | Roffman et al. |
| 5,968,094 A | 10/1999 | Werblin et al. |
| 6,126,283 A | 10/2000 | Wen et al. |
| 6,126,286 A | 10/2000 | Portney |
| 6,142,625 A | 11/2000 | Sawano et al. |
| 6,210,005 B1 | 4/2001 | Portney |
| 6,338,559 B1 | 1/2002 | Williams et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,609,793 B2 | 8/2003 | Norrby et al. |
| 6,705,729 B2 | 3/2004 | Piers et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,923,539 B2 | 8/2005 | Simpson et al. |
| 6,923,540 B2 | 8/2005 | Ye et al. |
| 6,986,578 B2 | 1/2006 | Jones |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,188,949 B2 | 3/2007 | Bandhauer et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,441,894 B2 | 10/2008 | Zhang et al. |
| 7,455,404 B2 * | 11/2008 | Bandhauer et al. ........... 351/168 |
| 7,475,986 B2 | 1/2009 | Dai et al. |
| 7,615,073 B2 | 11/2009 | Deacon et al. |
| 7,871,162 B2 | 1/2011 | Weeber |
| 2002/0118337 A1 | 8/2002 | Perrott et al. |
| 2003/0076478 A1 | 4/2003 | Cox |
| 2003/0171808 A1 | 9/2003 | Phillips |
| 2004/0021824 A1 | 2/2004 | Ye et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0230299 A1 | 11/2004 | Simpson et al. |
| 2005/0096226 A1 | 5/2005 | Stock et al. |
| 2005/0128432 A1 | 6/2005 | Altmann |
| 2005/0203619 A1 | 9/2005 | Altmann |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0176572 A1 | 8/2006 | Fiala |
| 2006/0238702 A1 | 10/2006 | Glick et al. |
| 2006/0244904 A1 | 11/2006 | Hong et al. |
| 2007/0052920 A1 | 3/2007 | Stewart et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0268158 A1 | 10/2009 | Weeber |
| 2009/0295295 A1 | 12/2009 | Shannon et al. |
| 2009/0323020 A1 | 12/2009 | Zhao et al. |
| 2010/0161048 A1 | 6/2010 | Schaper, Jr. |

FOREIGN PATENT DOCUMENTS

| | | |
|---|---|---|
| EP | 681198 A1 | 11/1995 |
| EP | 0926531 A1 | 6/1999 |
| EP | 949529 A2 | 10/1999 |
| EP | 1424049 A1 | 6/2004 |
| EP | 1310267 B1 | 1/2008 |
| EP | 1424049 B1 | 6/2009 |
| WO | WO9222264 A1 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | WO03009053 A1 | 1/2003 |
| WO | WO2004034129 A1 | 4/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO2006047698 A1 | 5/2006 |
| WO | WO2006060477 A2 | 6/2006 |
| WO | WO2006060480 A2 | 6/2006 |
| WO | WO2007092948 A1 | 8/2007 |
| WO | WO2007133384 A2 | 11/2007 |
| WO | WO2008045847 A2 | 4/2008 |
| WO | WO2009076670 A1 | 6/2009 |

OTHER PUBLICATIONS

International Search Report for Application No. PCT/US08/073999, mailed on Dec. 3, 2008, 3 pages.

International Search Report for Application No. PCT/US2010/061081, mailed on Apr. 6, 2011, 2 pages.

U.S. Appl. No. 12/129,155, filed Apr. 23, 2009.

U.S. Appl. No. 11/618,325, filed Dec. 29, 2006 (Brady et al).

U.S. Appl. No. 11/618,411, filed Dec. 29, 2006(Bradyetai).

U.S. Appl. No. 12/109,251, filed Apr. 24, 2008.

International Search Report and Written Opinion for Application No. PCT/IB2011/001067, mailed on Sep. 13, 2011, 13 pages.

Piers P.A., et al., "Eye Models for the Prediction of Contrast Vision in Patients with New Intraocular Lens Designs," Optics Letters, 2004, vol. 29 (7), pp. 733-735.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

Alfonso J.F., et al., "Prospective Study of the Acri.LISA bifocal Intraocular Lens," Journal of Cataract Refractive Surgery, 2007, vol. 33 (11), pp. 1930-1935.

Canovas C., et al., "Hybrid Adaptive-Optics Visual Simulator," Optical Letters, 2010, vol. 35 (2), pp. 196-198.

Cohen, Allen L., "Practical design of a bifocal hologram contact lens or intraocular lens," Applied Optics, 1992, 31 (19), 3750-3754.

Co-pending U.S. Appl. No. 12/771,550.

Diffractive Lenses for Extended Depth of Focus and Presbyopic Correction. Presentation from Wavefront Congress held on Feb. 15, 2008, Rochester, New York.

Doskolovich L.L., et al., "Special Diffractive Lenses," SPIE, 1992, vol. 1780, pp. 393-402.

International Search Report for Application No. PCT/EP2008/061235, mailed on Mar. 5, 2009, 4 pages.

International Search Report for Application No. PCT/EP2009/051783, mailed on Apr. 28, 2009, 3 pages.

International Search Report for Application No. PCT/US09/042449, mailed on Nov. 5, 2009, 5 pages.

International Search Report for Application No. PCT/US2010/038167, mailed on Sep. 27, 2010, 2 pages.

Liou H.L., et al., "Anatomically Accurate, Finite Model Eye for Optical Modeling," Journal of Optical Society of America, 1997, vol. 14 (8), pp. 1684-1695.

Marsack J.D., et al., "Metrics of Optical Quality Derived From Wave Aberrations Predict Visual Performance," Journal of Vision, 2004, vol. 4 (4), pp. 322-328.

Monsoriu J.A., et al., "Devil's Lenses," Optics Express, 2007, vol. 15 (21), pp. 13858-13864.

Norrby S., et al., "Model Eyes for Evaluation of Intraocular Lenses," Applied Optics, 2007, vol. 46 (26), pp. 6595-6605.

Piers P.A., et al., "Theoretical Comparison of Aberration-Correcting Customized and Aspheric Intraocular Lenses," Journal of Refractive Surgery, 2007, vol. 23 (4), pp. 374-384.

Siedlecki D., et al., "Radial Gradient index Intraocular Lens: a Theoretical Model," Journal of Modern Optics, 2008, vol. 55 (4-5), pp. 639-647.

Van Meeteren A., "Calculations on the Optical Modulation Transfer Function of the Human Eye for White Light," Optica Acta, 1974, vol. 21 (5), pp. 395-412.

Vanden Berg T.J., "Analysis of Intraocular Straylight, Especially in Relation to Age," Optometry and Vision Science, 1995, vol. 72 (2), pp. 52-59.

Villegas E.A., et al., "Correlation between Optical and Psychophy, Sical Parameters as a Function of Defocus," Optometry and Vision Science, 2002, vol. 79 (1), pp. 60-67.

* cited by examiner

DIFFRACTIVE MULTIFOCAL LENS HAVING RADIALLY VARYING LIGHT DISTRIBUTION

CROSS-REFERENCES TO RELATED APPLICATIONS

The present application is a divisional of application U.S. Ser. No. 12/109,251 filed on Apr. 24, 2008 (now U.S. Pat. No. 7,871,162), which incorporated by reference for all purposes the entire contents of: U.S. Provisional Application No. 60/047,699 entitled DIFFRACTIVE LENS EXHIBITING ENHANCED LIGHT DISTRIBUTION AND REDUCED SCATTER filed on Apr. 24, 2008.

BACKGROUND OF THE INVENTION

1. Field of the Invention

The present invention relates to ophthalmic lenses such as, for example, contact lenses or intraocular lenses (IOLs). Exemplary embodiments include monofocal and multifocal diffractive ophthalmic lenses having reduced light scatter and/or improved light energy distribution, for example, through subtle shaping of echelettes with appropriately curving profiles.

2. Description of Background Art

Presbyopia is a condition that affects the accommodation properties of the eye. As objects move closer to a young, properly functioning eye, the effects of ciliary muscle contraction and zonular relaxation allow the lens of the eye to change shape, and thus increase its optical power and ability to focus at near distances. This accommodation can allow the eye to focus and refocus between near and far objects.

Presbyopia normally develops as a person ages, and is associated with a natural progressive loss of accommodation. The presbyopic eye often loses the ability to rapidly and easily refocus on objects at varying distances. The effects of presbyopia usually become noticeable after the age of 45 years. By the age of 65 years, the crystalline lens has often lost almost all elastic properties and has only limited ability to change shape.

Along with reductions in accommodation of the eye, age may also induce clouding of the lens due to the formation of cataracts. Cataracts may form in the hard central nucleus of the lens, in the softer peripheral cortical portion of the lens, or at the back of the lens. Cataracts can be treated by the replacement of the cloudy natural lens with an artificial lens. An artificial lens replaces the natural lens in the eye, with the artificial lens often being referred to as an intra-ocular lens or "IOL".

A variety of technologies have been developed to enhance the ability of IOLs to facilitate viewing. Multifocal IOLs may, for example, often rely on a diffractive optical surface to direct portions of the light energy toward differing focal distances, thereby allowing the patient to clearly see both near and far objects. Alternative diffractive multifocal ophthalmic lenses (including contact lenses or the like) have been proposed for treatments of presbyopia without removal of the natural crystalline lens. Diffractive optical surfaces, either monofocal or multifocal, may also be configured to provide reduced chromatic aberrations.

Like other lenses, diffractive monofocal or multifocal lenses can make use of a material having a given refractive index and a surface curvature to provide a refractive power. Diffractive lenses also have a diffractive profile which confers the lens with a diffractive power that contributes to the overall optical power of the lens. The diffractive profile is typically characterized by a number of diffractive zones. The diffractive power is related to the properties of these zones, for instance their number, shape, size and position. When used for ophthalmic lenses these zones are typically annular lens zones, or echelettes, spaced about the optical axis of the lens. Each echelette may be defined by an optical zone, a transition zone between the optical zone and an optical zone of an adjacent echelette, and an echelette geometry. The echelette geometry includes a diameter and a shape or slope of the optical zone, as well as a height or step height of the transition zone. The diameters of the echelettes largely determine the power(s) of the lens and the step height of the transition zones largely determines the light distribution between the different add powers. Together, these echelettes form a diffractive profile, often saw-toothed or stepped, on one of the surfaces of the lens.

A multifocal diffractive profile of the lens can be used to mitigate presbyopia by providing two or more optical powers, for example, one for near vision and one for far vision. These lenses may be in the form of a multifocal contact lens, most commonly a bifocal contact lens. The lenses may also take the form of an intraocular lens placed within the capsular bag of the eye, replacing the original lens.

Although monofocal and multifocal diffractive ophthalmic lenses have greatly improved the quality of vision for many patients, additional improvements would still be beneficial. For example, some pseudophakic patients may experience scatter effects, such as halos. Therefore, monofocal and multifocal diffractive multifocal lenses having diffractive profiles resulting in reduced scatter (and thus an improved quality of vision) may be beneficial. For multifocal lenses, along with directing portions of the incident light energy at focal distances suitable for near and far viewing, diffractive optics may also direct significant light energy at other non-viewing foci, which can contribute to unwanted light-related visual phenomenon experienced by the patient (dysphotopsia). Having non-viewing foci of diffractive optics of multifocal lenses cannot be completely avoided. However, diffractive multifocal lenses having diffractive profiles which optimize the light energy distribution between viewing and non-viewing foci to improve quality of vision would also be beneficial. Controllably varying light distributions over the diffractive profile may also provide some advantages, so that diffractive multifocal lenses having diffractive profiles which vary light distribution over the profile may be desirable.

BRIEF SUMMARY OF THE INVENTION

The present invention generally provides improved lenses and imaging techniques. Embodiments of the present invention provide improved ophthalmic lenses (including, for example contact lenses, intraocular lenses (IOLs), and the like) and associated methods for their design and use. Exemplary embodiments provide monofocal and/or multifocal diffractive ophthalmic lenses having reduced light scatter and/or improved light energy distribution, for example, through subtle shaping of echelettes with appropriately curving profiles extending between the optical zones of adjacent echelette surfaces. In some embodiments, diffractive ophthalmic lenses having multiple foci often use a zero order diffraction for far vision and a first order diffraction for near vision, while limiting the light energy directed to the other unwanted orders. Specifically, it has been recognized that light energy directed to foci of a selected subset of the non-viewing orders—those that are closest to the zero order focus—can have an disproportionate effect on vision quality. By limiting the light energy in such selected orders (optionally, even at the cost of directing more total light energy to higher and/or non-viewing order foci), dysphotopsia may be mitigated. Imposing a controlled curvature across a series of echelettes can be used to tailor energies of the various foci or diffraction orders so as to provide such benefits, and/or may be used to limit scatter effects which may otherwise be generated by the sharp corners associated with vertical steps between adjacent conventional diffractive echelettes.

In a first aspect, the invention provides a multifocal ophthalmic lens. The ophthalmic lens includes an anterior face and a posterior face. Each face has a refractive profile. The faces are disposed about an optical axis. The faces may define a clear aperture. A diffractive profile is imposed on one of the refractive profiles. The diffractive profile includes a plurality of echelettes with associated step heights that are substantially equal to one another. The diffractive profile has, in the visible waveband, a zeroth diffractive order and a first diffractive order having a diffraction add power. The zeroth and first diffraction orders have diffraction efficiencies which change with radius from the optical axis.

In many embodiments, the diffractive profile is characterized by a continuous function over a plurality of echelettes.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffraction orders have diffraction efficiencies which change with the number of surrounding echelettes. In some embodiments N is at least 4. The zeroth and the first diffraction orders have diffraction efficiencies which change depending on the number of surrounding echelettes.

In another aspect, the invention provides a multifocal ophthalmic lens. The ophthalmic lens includes an anterior face and a posterior face. Each face has a refractive profile. The faces are disposed about an optical axis. The faces may define a clear aperture. A diffractive profile is imposed on one of the refractive profiles. The diffractive profile includes a plurality of echelettes with associated step heights that are substantially equal to one another. The diffractive profile has, in the visible waveband, a first diffractive order and a second diffractive order having a diffraction add power. The first and second diffraction orders have diffraction efficiencies which change with radius from the optical axis.

In many embodiments, the diffractive profile is characterized by a continuous function over a plurality of echelettes.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffraction orders have diffraction efficiencies which change with the number of surrounding echelettes. In some embodiments N is at least 4. The first and the second diffraction orders have diffraction efficiencies which change depending on the number of surrounding echelettes.

In another aspect, the invention provides a method for viewing with a diffractive ophthalmic lens using an eye of a patient. The ophthalmic lens includes a plurality of echelettes with associated step heights that are substantially equal to one another. The echelettes each have a characteristic profile and define a diffractive surface. The diffractive surface has in the visible waveband, a zeroth diffractive order and a first diffractive order. The method comprises changing the diffractive efficiency of the first diffractive order of the echelettes with radius from the optical axis.

In many embodiments, changing the diffractive efficiency of the first diffractive order of each of the echelettes with radius from the optical axis comprises changing the profile of each of the echelettes with radius from the optical axis.

In many embodiments, the echelettes comprise a central echelette and N additional echelettes. The N additional echelettes comprise a first echelette disposed about the central echelette, a second echelette disposed about the first echelette, up to an Nth echelette disposed about an (N−1)th echelette. In some embodiments, the zeroth and first diffraction orders have diffraction efficiencies which change with the number of surrounding echelettes. In some embodiments N is at least 4. The zeroth and the first diffraction orders have diffraction efficiencies which change depending on the number of surrounding echelettes.

In many embodiments, any one of the step heights do not vary by more than 20 percent from an average of all the step heights.

BRIEF DESCRIPTION OF THE DRAWINGS

For illustration purposes, the profile geometries shown in the aforementioned figures were not drawn exactly to scale. The heights of the diffractive profiles shown in the figures is generally in the order of about 0.5 millimeters and about 2.0 millimeters although the heights may vary depending on factors such as the amount of correction needed by the patient, the refractive index of the lens material and surrounding medium, and the desired distribution of light between wanted diffraction orders.

DETAILED DESCRIPTION OF THE INVENTION

The present invention generally provides improved lenses and imaging systems. Embodiments of the invention may find their most immediate use may be in the form of improved ophthalmic devices, systems, and methods. Exemplary embodiments of the present invention provide improved ophthalmic lenses (including, for example contact lenses, intraocular lenses (IOLs), corneal lenses and the like) and associated methods for their design and use. Embodiments of the present invention include monofocal diffractive lenses, bifocal diffractive lenses, and multifocal diffractive lenses. Exemplary embodiments provide multifocal diffractive ophthalmic lenses having reduced light scatter and/or improved light energy distribution so as to enhance viewing performance, for example, through subtle shaping of a smoothly curving profile extending across a plurality of echelettes. The surface is generally optically smooth to help reduce scatter. As used herein, "optically smooth" means having an average roughness that is much smaller than the wavelength of visible light (e.g., having an rms roughness that is less that 100 nm, $\lambda/10$, or the like, where $\lambda$ is a wavelength of light).

Diffractive ophthalmic lenses having multiple foci often use zero order diffraction for far vision and first order diffraction for near vision. Some portion of the light energy is also directed to other, non-viewing orders. As used herein, the term "non-viewing order" means a diffractive order containing energy that is not useful in forming an image on the retina of an eye. By recognizing that foci of the non-viewing orders that are closest to the zero order focus can have the largest negative effect on vision quality, and by limiting the light energy in such selected non-viewing orders, dysphotopsia (e.g., scattering or halo effects) may be mitigated, even if more total cumulative light energy ends up being directed to higher order and/or other non-viewing foci. Imposing a controlled shape or curvature across a plurality of echelettes can be used to tailor energies of the various foci so as to provide such benefits, and may also be used to limit deleterious scatter that can otherwise be generated by the sharp corners associated with vertical steps between adjacent conventional diffractive echelettes.

The shape or diffractive profile of a multifocal lens can impact the light energy distribution between foci. For example, known multifocal lenses often seek to distribute imaging light energy between 2 viewing foci: one (typically the zero order focus) corresponding with far viewing distances and one (typically the first order focus) corresponding to near viewing distances. The remaining light is distributed to other non-viewing foci. For example, a conventional multifocal lens with a desired 50%:50% light distribution between the far and near foci, may also result in about 41% of the light energy directed to the far focus, about 41% of the light energy directed to the near focus, and about 18% of the light energy being directed to non-viewing and/or higher order foci, the higher order foci being generally situated symmetrically around the 2 main viewing foci. In order of diminishing brightness, the next brightest foci may, for example, be the $-1^{st}$ and $2^{nd}$ order foci, each of which are non-viewing foci and may receive about 4.5% of the light energy.

The non-viewing and/or higher order foci have a negative effect on the quality of vision. However, the negative effect of the various non-viewing foci will not be the same, and will not depend solely on the portion of incident light energy each focus receives. Instead, higher order foci that are close to the zero order focus will tend to have a disproportionately larger negative effect on perceived scatter and halo effects. Too much light energy (and thus brightness) in such higher order foci can contribute to dysphotopsia. Therefore, diffractive multifocal lenses having diffractive profiles which optimize and/or selectively tailor the light energy distribution between the various foci may improve quality of vision and reduce dysphotopsia for pseudophakic patients, contact lens users, and the like.

The structures of the present invention may also present additional advantages by enhancing the design flexibility through selectively curving echelette profiles, with the curvatures presenting additional design variables that can be used to benefit overall viewing performance. For example, varying light distributions over the diffractive profile may also provide advantages. Reading is often done in bright light conditions in which the pupil is small. In contrast, night-time driving is done in low light conditions in which the pupil is large. It may be advantageous to vary light distribution radially across the diffractive profile so that different light energy splits are provided based on the viewing situation and resulting pupil size. In some such ophthalmic lenses, a greater proportion of light energy may be transmitted to the far focus from a peripheral portion of the lens to accommodate for low light, far viewing conditions such as night time driving, with the near viewing receiving relatively more light energy from a central portion of the diffractive profile. Varying curvature and/or shapes of the echelettes radially may thus provide diffractive multifocal lenses having a diffractive profiles which vary light distribution over the profile as the pupil changes in size.

As another example of the benefits of intentional and controlled curving diffractive profiles for ophthalmic lenses, the scatter of multifocal diffractive lenses may be higher than that of corresponding monofocal and/or purely refractive designs. The diffractive profile of multifocal diffractive lenses may play a significant role in producing such scatter, and appropriately controlled curving profiles may be employed to inhibit such scatter, often providing such benefits in combination with one or more of the other improvements described herein.

Figure 1A:
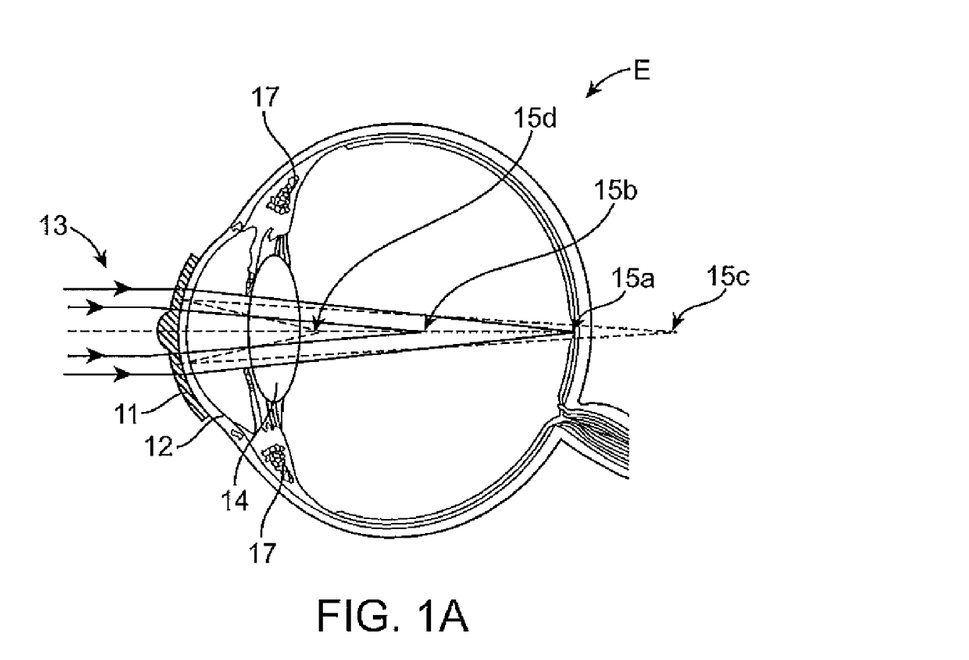
FIG. 1A is a cross-sectional view of an eye with a multifocal contact lens.

FIG. 1A is a cross-sectional view of an eye E fit with a multifocal contact lens 11. Multifocal contact lens 11 may, for example, comprise a bifocal contact lens. Multifocal contact lens 11 covers at least a portion of cornea 12 at the front of eye E and is generally centered about the optical axis of eye E.

Each major face of lens 11, including the anterior (front) surface and posterior (back) surface, generally has a refractive profile. The two surfaces together, in relation to the properties of the air, tear film, cornea, and other optical components of the overall optical system, define the effects of the lens 11 on the imaging performance by eye E. Conventional, monofocal contact lenses have a refractive power based on the refractive index of the material from which the lens is made, and also on the curvature or shape of the front and mar surfaces or faces of the lens.

In a young, healthy eye contraction and relaxation of ciliary muscles 17 surrounding the natural lens 14 contribute to accommodation of the eye, the process by which the eye increases optical power to maintain focus on objects as they move closer. As a person ages, the degree of accommodation decreases and presbyopia, the diminished ability to focus on near objects, often results. A patient may therefore need corrective optics having two optical powers, one for near vision and one for far vision, as provided by multifocal contact lens 11.

Multifocal lenses may optionally also make use of the refractive properties of the lens. Such lenses generally include different powers in different regions of the lens so as to mitigate the effects of presbyopia. For example, as shown in FIG. 1A, a perimeter region of refractive multifocal lens 11 may have a power which is suitable for viewing at far viewing distances. The same refractive multifocal lens 11 may also include an inner region having a generally higher overall power (sometimes referred to as a positive add power) suitable for viewing at near distances.

Rather than relying entirely on the refractive properties of the lens, multifocal diffractive contact lenses or IOLs can also have a diffractive power. The diffractive power can, for example, comprise positive add power, and that add power may be a significant (or even the primary) contributor to the overall optical power of the lens. The diffractive power is conferred by a plurality of concentric diffractive zones which form a diffractive profile. The diffractive profile may either be imposed on the anterior face or posterior face or both.

The diffractive profile of a diffractive multifocal lens acts as a diffraction grating and directs incoming light into a number of diffraction orders. As light 13 enters from the front of the eye, multifocal contact lens and the natural lens 14 bend light 13 to form a far field focus 15a on retina 16 for viewing for distant objects and a near field focus 15b for objects close to the eye. Depending on the distance form the source of light 13, the focus on retina 16, the viewing focus, may be near field focus 15b instead. Far field focus 15a is associated with $0^{th}$ diffractive order and near field focus 15b is associated with the $1^{st}$ diffractive order.

Multifocal ophthalmic lens 11 typically distributes the majority of light energy into the two viewing orders, often with the goal of splitting imaging light energy evenly (50%: 50%). However, a significant portion of the incident light energy is directed into other, non-viewing diffractive orders 15c, 15d, and the like (the non-viewing orders typically comprising the $2^{nd}$, $3^{rd}$, ..., $-1^{st}$, $-2^{nd}$, $-3^{rd}$, ...) such that the $0^{th}$ and $1^{st}$ order each receive about 40.5% of the light energy when standard ideal parabolic echelettes with sharp vertical transitions are used. The remaining percentage of the light energy is received by the higher and lower orders, with the $-1$ and $2^{nd}$ order each receiving about 4.5% of the light energy for such lenses.

Figure 1B:
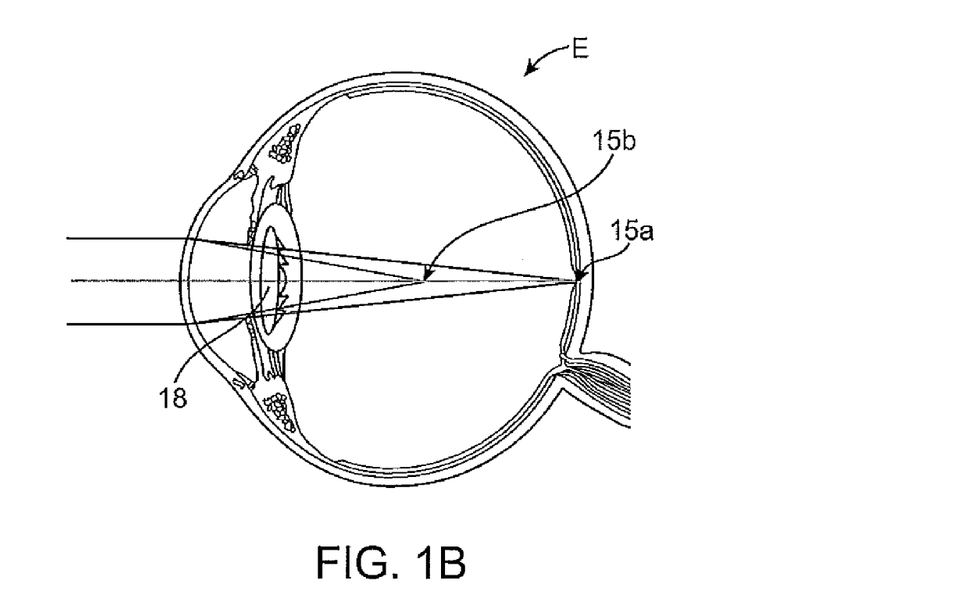
FIG. 1B is a cross-sectional view of an eye having an implanted multifocal intraocular lens.

The corrective optics may also be provided by other types of multifocal ophthalmic lenses such as multifocal intraocular lens (IOL) 18 shown in FIG. 1B. For patients with IOLs, natural lens 14 is removed and IOL 18 is placed within capsular bag 19 in eye E. IOL 18 is centered about the optical axis of the eye E. Like multifocal contact lens 11, IOL 18 often has a refractive power and a diffractive power from a number of concentric diffractive zones. Likewise, IOL 18 focuses incoming light 13 to far field focus 15a and near field focus 15b.

Figure 2A:
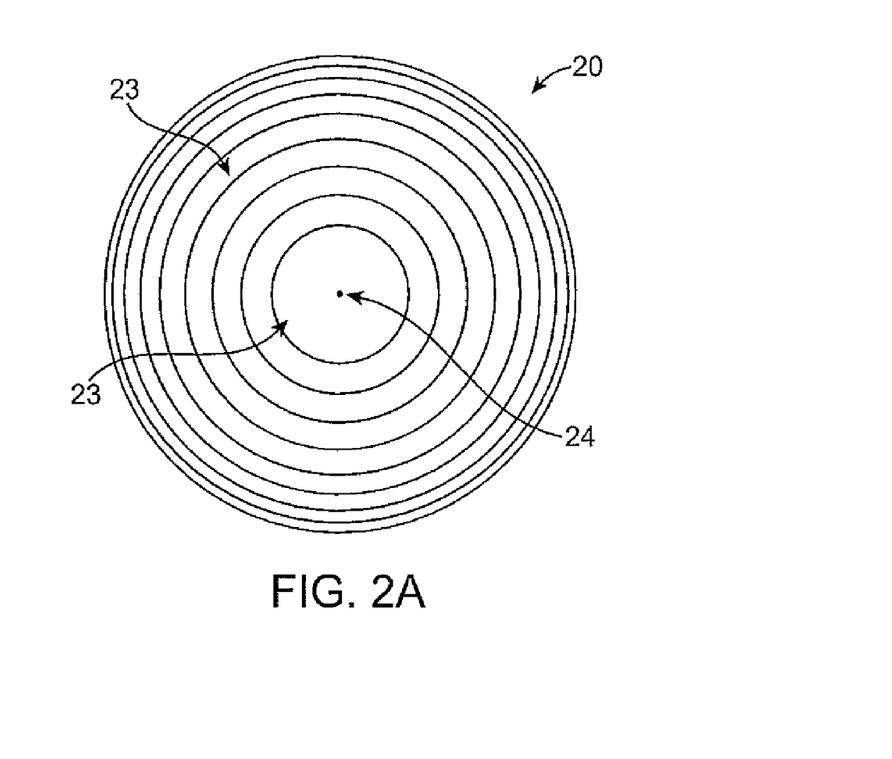
FIG. 2A is a front view of a multifocal ophthalmic lens.
Figure 2B:
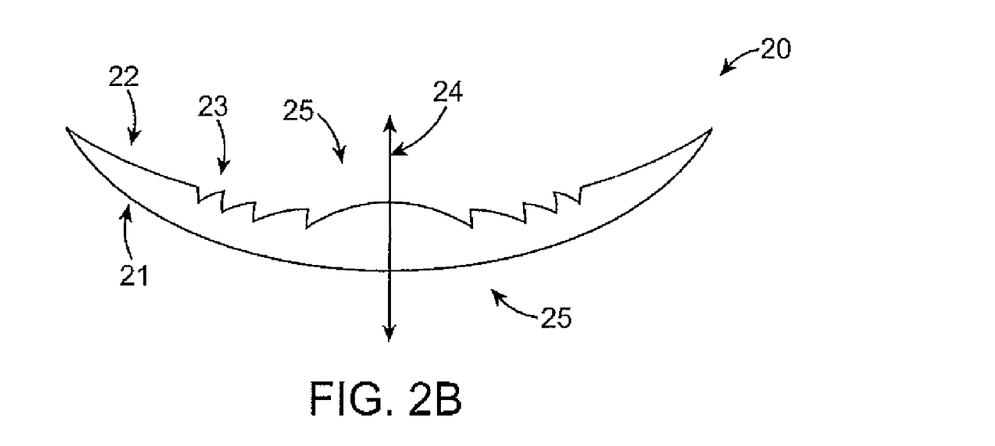
FIG. 2B is a cross-sectional view of the lens of FIG. 2A.

FIGS. 2A and 2B show an exemplary multifocal lens 20. Multifocal lens 20 has optical properties that may be generally similar to those of multifocal contact lens 11 and IOL 18 described above. Multifocal lens 20 has an anterior lens face 21 and a posterior lens face 22 disposed about optical axis 24. The faces 21, 22 of lens 20 typically define a clear aperture 25. As used herein, the term "clear aperture" means the opening of a lens or optic that restricts the extent of a bundle of light rays from a distant source that can imaged or focused by the lens or optic. The clear aperture is usually circular and is specified by its diameter.

When fitted onto the eye of a subject or patient, the optical axis of lens 20 is generally aligned with the optical axis of eye E. The curvature of lens 20 gives lens 20 an anterior refractive profile and a posterior refractive profile. Although a diffractive profile may also be imposed on either anterior face 21 and posterior face 22 or both, FIG. 2B shows posterior face 22 with a diffractive profile. The diffractive profile is characterized by a number of annular optical zones or echelettes 23 spaced about optical axis 24.

Figure 3A:
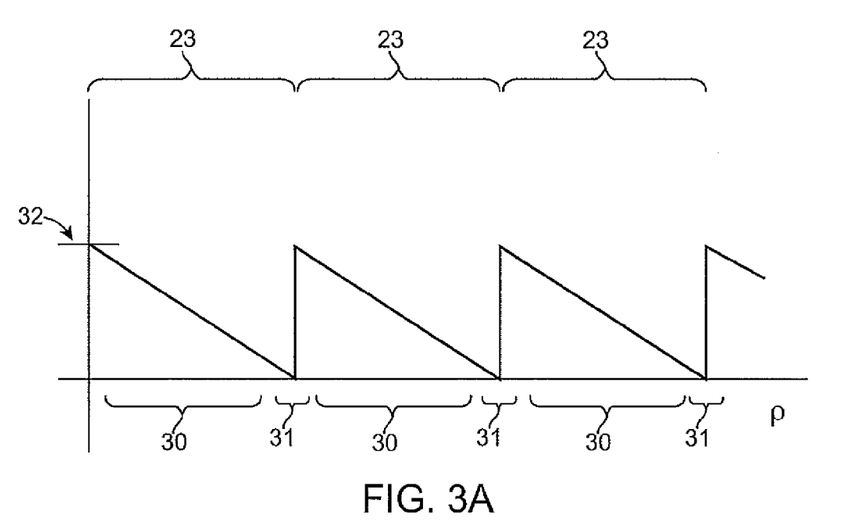
FIG. 3A-3B are graphical representations of a portion of the diffractive profile of a conventional multifocal lens.
Figure 3B:
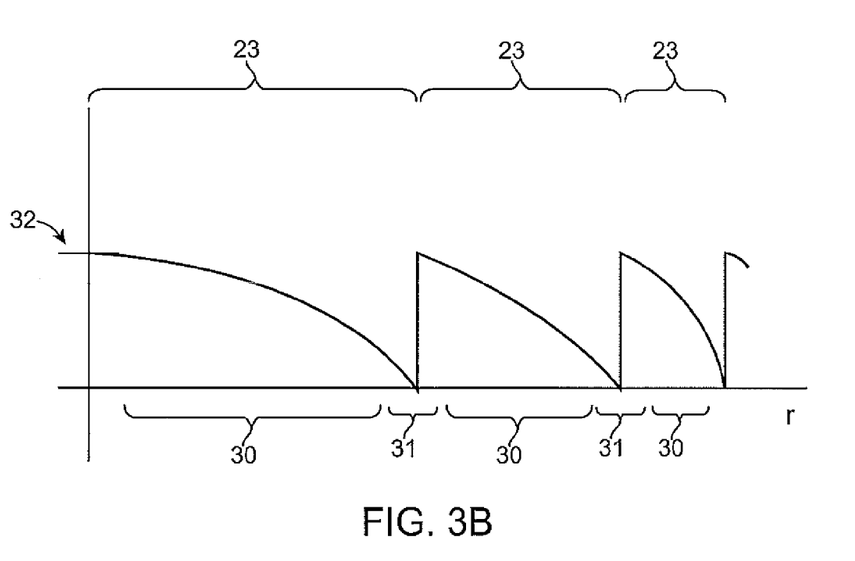

FIGS. 3A and 3B are graphical representation of a portion of the diffractive profile of conventional or reference multifocal lens 20. In FIG. 3A, the displacement (from the optical axis or another reference point on a plane perpendicular to the optical axis) of each point on the echelette surface is plotted against the square of the radial distance ($r^2$ or p) from the optical axis of the lens. In conventional multifocal lenses, each echelette 23 may have a diameter or distance from the optical axis which is often proportional to √n, n being the number of the echelette 23 as counted from optical axis 24. Each echelette has a characteristic optical zone 30 and transition zone 31. Optical zone 30 has a shape or downward slope that may be linear when plotted against ρ as shown in FIG. 3A. When plotted against radius r, optical zone 30 has a shape or downward slope that is parabolic as shown in FIG. 3B. The shape or slope of optical zone 30 determines the add power of lens 20.

As shown in FIGS. 3A and 3B, transition zone 31 between adjacent echelettes is generally sharp and discontinuous. The height of the lens face sharply transitions from sloping steadily downwards to stepping vertically upwards, and the transitions abruptly back to sloping steadily downwards again. In doing so, echelettes 23 also have a characteristic step height 32 defined by the distance between the lowest point and height point of the echelette. Hence, the slope (or first derivative) and/or the curvature (second derivative) of the diffractive surface are discontinuous adjacent the transitions.

The light energy distribution between different diffractive orders is dependent on a wavelength λ, often in the visible band, the depth of step height 32, and the difference ($\Delta\eta$) between the refractive index of the lens and that of the surrounding medium. For example, step height 32 having a depth of λ will distribute the majority of light energy to the $1^{st}$ order, which corresponds to the near field, and essentially be monofocal. At a depth of greater than $\lambda/(2\Delta\eta)$, there will be greater light energy or intensity distributed to the $1^{st}$ order than the $0^{th}$ order, which corresponds to the far field. At a depth of less than $\lambda/(2\Delta\eta)$, light energy is distributed more towards the $0^{th}$ order. Most commonly, a depth of $\lambda/(2\Delta\eta)$ is used for conventional multifocal lenses. At this depth, light energy at the wavelength λ can be distributed evenly between the $1^{st}$ and $0^{th}$ orders, often at 40.5% each with the $-1^{st}$ and $2^{nd}$ orders each receiving 4.5% of the light energy.

Figure 4A:
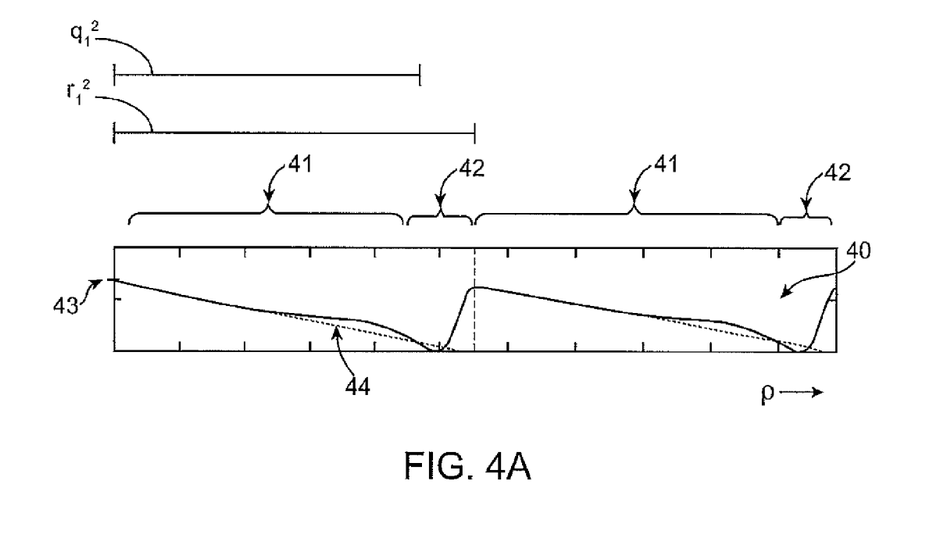
FIG. 4A is a graphical representation of a portion of the diffractive profile of a multifocal lens according to embodiments of the present invention.

FIG. 4A is a graphical representation of a portion of the diffractive profile of a multifocal lens according to an exemplary embodiment of the present invention. The diffractive profile 40 provided by the present invention is generally similar to those shown by FIG. 3A-3B. A multifocal ophthalmic lens with profile 40 is generally similar to the lens shown by FIGS. 2A-2B. Again, the height of each point on the echelette surface is plotted against the square of the radial distance ($r^2$ or ρ) from the optical axis of the lens. However, diffractive profile 40 has smooth, continuously curving transition zones 42 between optical zones 41. The smooth, continuous profile reduces the amount of light scatter both by eliminating discontinuities and by reducing the energy in certain predetermined non-viewing orders. Because scatter occurs as a result of light encountering an object (for example, an edge, discontinuity, or in this case, a transition zone) which as the size of about one wavelength of the light, scatter can be reduced by having the radii of curvature of the transition zones larger than the wavelength of incoming light. The total area of the optical zone and smooth transition zone as well as a characteristic step height 43 contribute to the light energy distribution properties of the lens.

The methods described to reduce scatter and optimize light energy distribution are not limited in application to multifocal diffractive lenses. They may also be applicable to monofocal diffractive lenses, for example, those described in U.S. Pat. No. 6,830,332, which is herein incorporated by reference. Monofocal diffractive lenses include a refractive portion and a monofocal diffractive portion. The diffractive portion has a single viewing focus. Implementing a smooth, transition zone having a radius of curvature greater than a design wavelength λ would also reduce scatter resulting from the transition zones of the diffractive portion of the monofocal lens. Light distribution may also be balanced between the viewing focus and non-viewing foci using the methods described.

Diffractive profile 40 is shown with a filled line compared to a conventional diffractive profile 44 shown with a parabolic profile shown with a dotted line. The exemplary diffractive profile is defined by a single, continuous function. In other embodiments, the optical zone and the transition zone may each be defined by distinct functions. The single, continuous function shown is a cosine function enhanced by a power function and a stretch function. The function, Equation 1, is as follows:

$$\Delta(\rho) := \Delta_0 \cdot \left[ \left[ 1 - \left( \frac{\rho}{r_1^2} \right)^{en} \right] \cdot \left[ 1 - \left( \frac{\rho}{r_1^2} \right) \right] + \left[ \left( \left( \frac{\rho}{r_1^2} \right) \right)^{en} \right] \cdot \right.$$
$$\left[ 0.5 + 0.5 \cdot \cos \left[ \pi \frac{\rho}{q_1^2} [1.0 + (\rho - q_1^2) \cdot [Y\_min + \right.\right.$$
$$\left.\left.\left. (Y\_max - Y\_min) \cdot \left[ 0.5 \cdot \tanh \left[ \frac{(\rho - X\_shift)}{m} \right] + 0.5 \right] \right] \right] \right]$$

$\Delta(\rho)$ is the displacement from a reference plane perpendicular to the optical axis, in other words the height of the profile at a position $\rho$; $\rho$ is the square of radius r from the optical axis; en is an exponential power; $r_1$ is a radius of the first or central echelette; $q_1$ is the size of the optical zone of the first or central echelette ($r_1 - q_1$ would therefore be the size of the transition zone); Y_min is a parameter that determines the shape of the optical zone; Y_max is $(2q_1^2 - r_1^2)/(r_1^2 - q_1^2)/r_1^2$; X_shift is $q_1^2$; in is a parameter indicative of the width of a region blending the optical zone (for the first optical zone, this is when $r < q_1$) and the transition zone (for the first optical zone, this is when $r > q_1$); and $\Delta_0$ is the height of the profile. It will be noted that the term $[1-(\rho/r_1^2)^{en}][1-(\rho/r_1^2)]$ in this equations is an optical zone term that decreases as $\rho$ increases, while the remaining variables to the right of this term form a transition zone term. The addition of optical zone term and the transition term gives the shape of the continuous of the profile.

The exemplary diffractive profile 40 is characterized by the above function wherein α=0.592, en=3, r1/q1=0.95, m=1 and Y_min=−0.0002.

In addition to reducing the amount of scatter, diffractive profile 40 results in a different light energy distribution to the diffractive orders, as shown below in Table 1. Compared to a conventional, parabolic diffractive profile which distributes 81.1% of the light energy to the $0^{th}$, and $1^{st}$ orders, diffractive profile 40 distributes less overall energy—here 79.1% of the light energy—to the $0^{th}$ and 1 orders. Also, conventional diffractive profiles distributes 4.5% of the light to the $-1^{st}$ order, the non-viewing order closest to the far focus (i.e., the diffraction efficiency of the −1 order is 4.5%). In contrast, diffractive profile 40 distributes less that 4%, often being less than 3%, and preferably less that 2.5% of the incident light energy to the $-1^{st}$ order, with the exemplary embodiment delivering only 2.1% of the light energy (i.e., the diffraction efficiency of the −1 order is 2.5%) to the $-1^{st}$ order. This results in less disturbance in far field vision, improving far field quality of vision and reducing dysphotopsia to a lower level.

TABLE 1

| Order | % Light Energy |
|---|---|
| −3 | 2.1% |
| −2 | 2.5% |
| −1 | 2.1% |
| 0 | 39.6% |
| 1 | 39.5% |
| 2 | 6.5% |
| 3 | 1.1% |

Figure 4B:
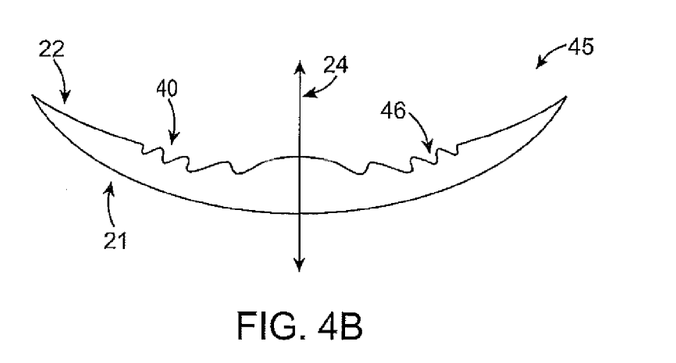
FIG. 4B is a cross-sectional view of a multifocal ophthalmic lens having the diffractive profile shown by FIG. 4A.

FIG. 4B schematically shows a multifocal ophthalmic lens 45 having diffractive profile 40 of FIG. 4A. Like the conventional ophthalmic lens 20 of FIG. 2B, multifocal ophthalmic lens 45 has an anterior lens face 21 and a posterior lens face 22, each having a refractive profile based on its curvature and material from which it is made. The lens faces are disposed about optical axis 24 and define a clear aperture 25. Diffractive profile 40 is imposed on posterior lens face 22. Diffractive profile 40 is defined by a number of echelettes 46 concentrically spaced about optical axis 24.

Figure 5A:
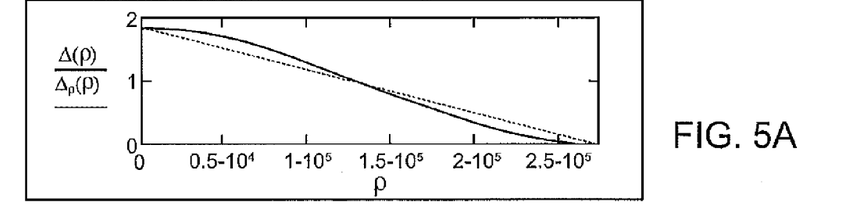
FIGS. 5A through 5I show graphs of diffractive profiles of multifocal lenses according to embodiments of the present invention.
Figure 5B:
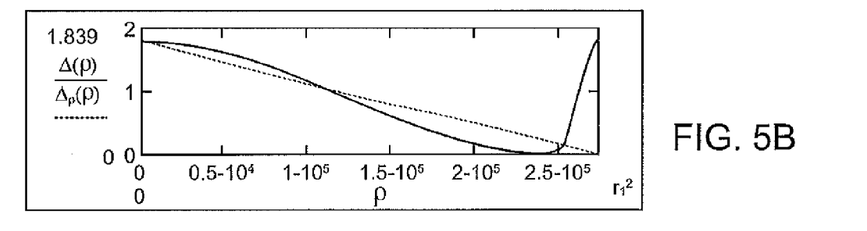
Figure 5C:
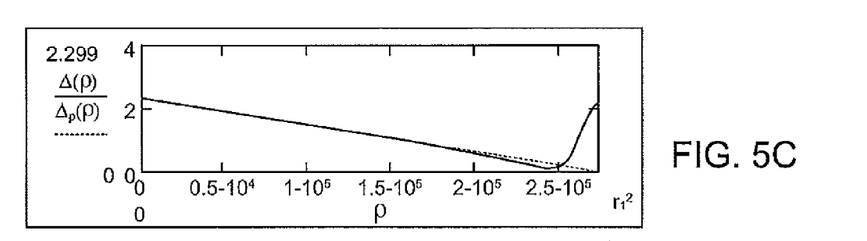
Figure 5D:
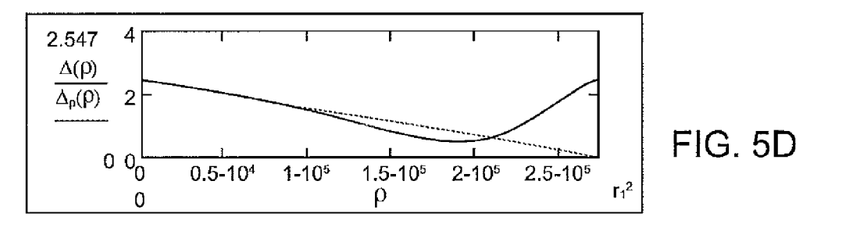
Figure 5E:
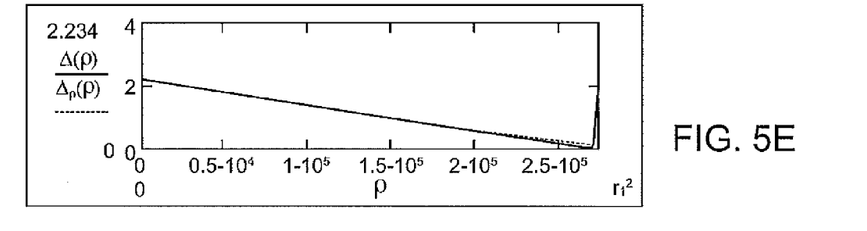
Figure 5F:
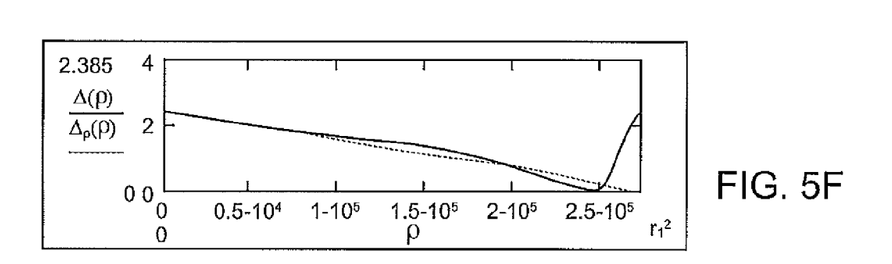
Figure 5G:
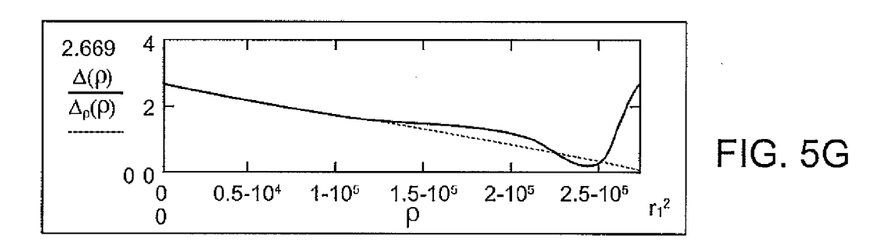
Figure 5H:
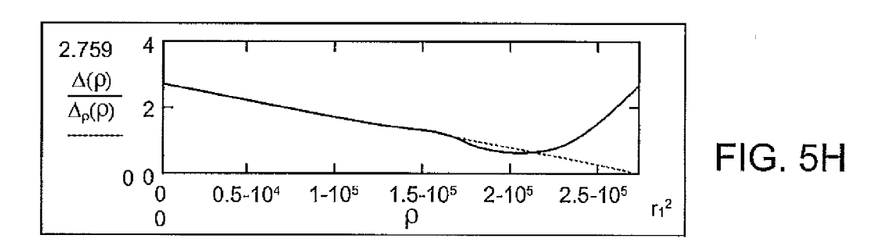
Figure 5I:
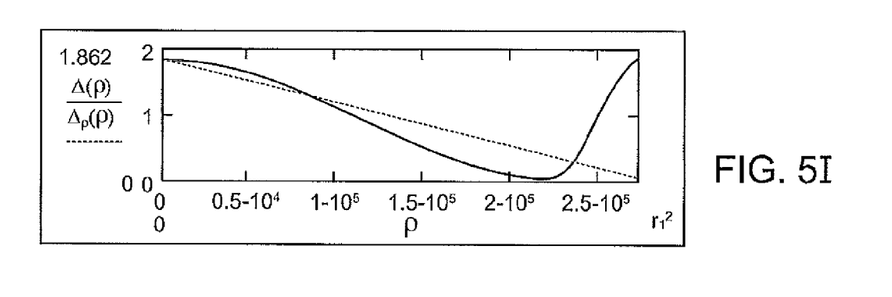

FIGS. 5A through 5I shows graphs of diffractive profiles according to Equation 1 computed with the parameters shown below in Table 2. Table 2 shows the light distribution per diffractive order for the various diffractive profiles shown by FIGS. 5A-5I. FIG. 5A shows profile code 0-2 from the table, FIG. 5B shows profile code 0-3, FIG. 5C shows profile code 4-1; FIG. 5D shows profile code 4-2; FIG. 5E shows profile code 4-3; FIG. 5F shows profile code 4-4; FIG. 5G shows profile code 4-5; FIG. 5H shows profile code 4-6; FIG. 5I shows profile code 4-7. FIGS. 5A through 5I also include the conventional diffractive profile (code 0-1 in Table 2) shown as a dotted line.

Profile 4-5 corresponding to diffractive profile 40 of FIG. 4 has a diffraction efficiency of the −1 order of 2.1%. Profile 0-1 corresponding to a conventional parabolic profile has a diffraction efficiency of the −1 order of 4.5%. Although not shown, other parameters used for function 1 may result in profiles other than profile 4-5 having a diffraction efficiency of the −1 order of less than 4.5%, preferably less than 4%, and more preferably less than 2.5%.

TABLE 2

| | Profile Code | | | | | | | | | |
|---|---|---|---|---|---|---|---|---|---|---|
| Order | 0-1 Parabolic | 0-2 Parabolic with Cosine ending | 0-3 Parabolic with Cosine ending | 4-1 Parabolic with Cosine ending | 4-2 Parabolic with Cosine ending | 4-3 Parabolic with Cosine ending | 4-4 Parabolic with Cosine ending | 4-5 Parabolic with Cosine ending | 4-6 Parabolic with Cosine ending | 4-7 Parabolic with Cosine ending |
| −3 | 0.8% | 1.0% | 1.8% | 1.9% | 2.2% | 1.0% | 2.0% | 2.1% | 3.0% | 2.0% |
| −2 | 1.6% | 2.3% | 3.6% | 3.1% | 6.2% | 1.9% | 3.3% | 2.5% | 6.4% | 4.7% |
| −1 | 4.5% | 7.9% | 10.9% | 5.8% | 15.6% | 4.7% | 4.5% | 2.1% | 10.3% | 14.2% |
| 0 | 40.5% | 40.3% | 39.6% | 40.3% | 37.3% | 40.6% | 39.5% | 39.6% | 38.8% | 38.6% |

TABLE 2-continued

| | | | | | Profile Code | | | | | |
|---|---|---|---|---|---|---|---|---|---|---|
| Order | 0-1 Parabolic | 0-2 Parabolic with Cosine ending | 0-3 Parabolic with Cosine ending | 4-1 Parabolic with Cosine ending | 4-2 Parabolic with Cosine ending | 4-3 Parabolic with Cosine ending | 4-4 Parabolic with Cosine ending | 4-5 Parabolic with Cosine ending | 4-6 Parabolic with Cosine ending | 4-7 Parabolic with Cosine ending |
| 1 | 40.5% | 40.2% | 39.6% | 40.3% | 37.4% | 40.5% | 39.5% | 39.5% | 38.9% | 38.5% |
| 2 | 4.5% | 2.0% | 0.7% | 3.2% | 0.1% | 4.3% | 5.2% | 6.5% | 0.3% | 0.0% |
| 3 | 1.6% | 1.0% | 0.4% | 0.5% | 0.2% | 1.4% | 0.5% | 1.1% | 0.2% | 0.1% |
| | | | | | Parameters | | | | | |
| α | 0.5 | 0.405 | 0.408 | 0.5115 | 0.565 | 0.4955 | 0.529 | 0.592 | 0.621 | 0.413 |
| en | n/a | n/a | 0 | 4 | 2 | 10 | 2 | 3 | 5 | 0 |
| $r_1/q_1$ | n/a | n/a | 0.95 | 0.95 | 0.8 | 0.99 | 0.95 | 0.95 | 0.81 | 0.9 |
| m | n/a | n/a | 1 | 1 | 1 | 1 | 1 | 1 | 1 | 1 |
| Y_min | n/a | n/a | 0 | 2.5E−6 | 0 | 0 | 5E−06 | −2E−05 | 4E−05 | 2E−08 |

Figure 6A:
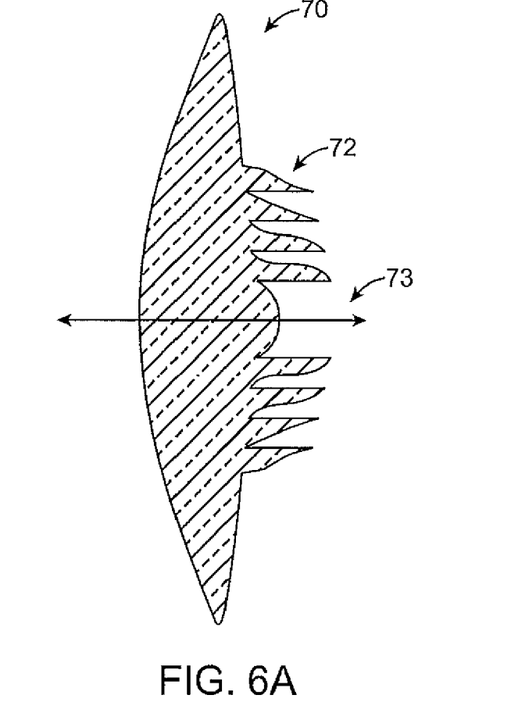
FIG. 6A is a cross-sectional view of a multifocal lens according to embodiments of the present invention having constant step height of the transition zones and varying shapes of the optical zones with radius.
Figure 6B:
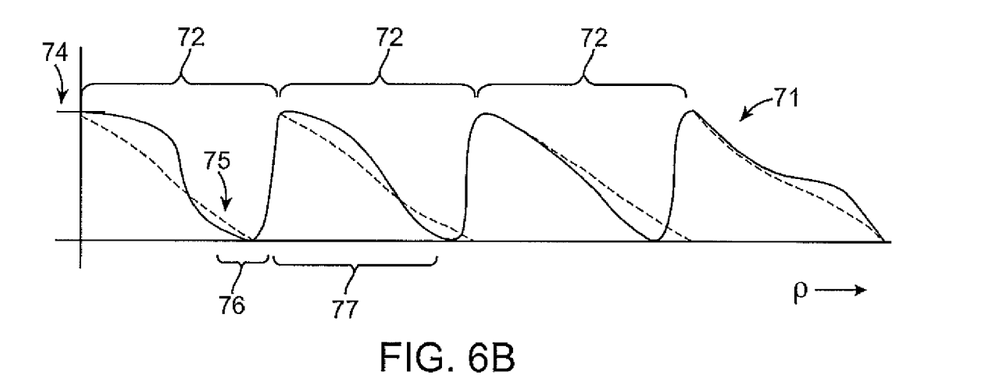
FIG. 6B is a graphical representation of the diffractive profile of the lens of FIG. 7A, FIG. 7A-7D show graphs of the diffractive profiles of individual echelettes according to embodiments of the present invention.
Figure 7A:
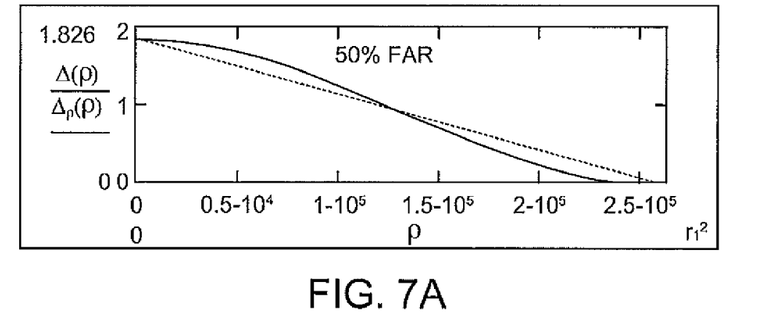
Figure 7B:
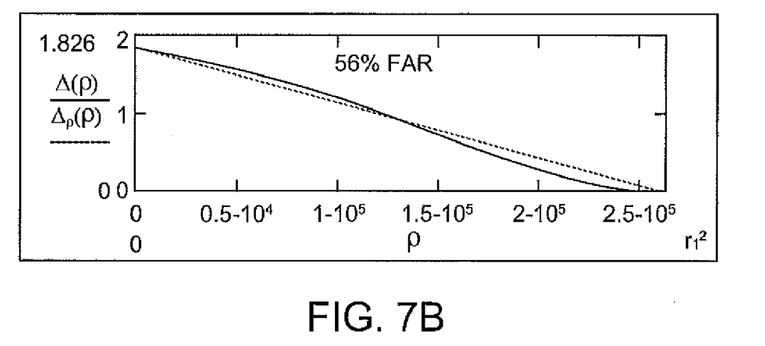
Figure 7C:
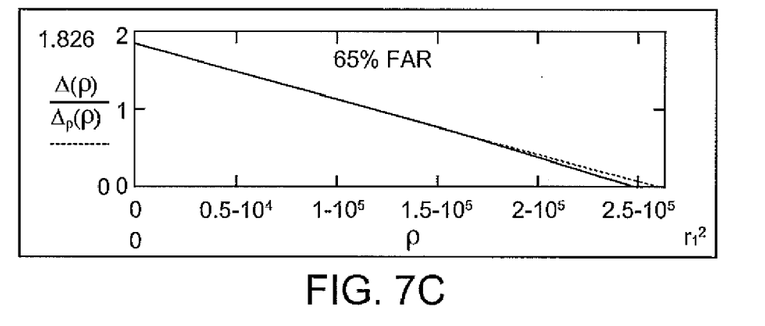
Figure 7D:
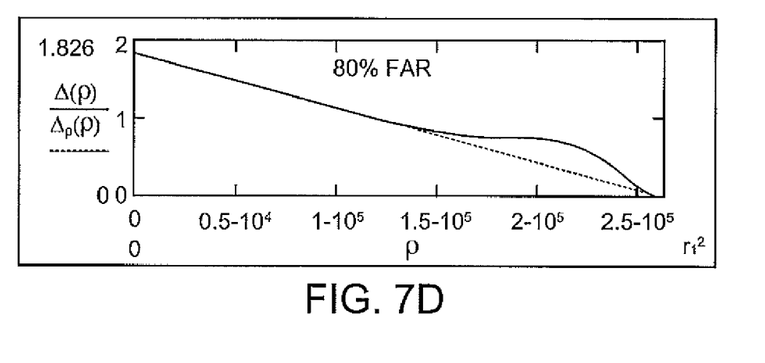

FIG. 6A shows a cross-sectional view of an alternative multifocal ophthalmic lens 70. Like previously described multifocal, ophthalmic lenses, lens 70 comprises a number of echelettes 72 spaced about optical axis 73. Echelettes 72 each have an optical zone and a transition zone. Echelettes 72 of lens 70 each share a common step height 74. However, as seen in FIG. 6B, each echelette 71 has a different shape, which changes the diffractive efficiency of each echelette. Hence, lens 70 may provide pupil-dependent variable imaging energy distribution similar to that of variable step height or apodization (including those described in U.S. Pat. No. 5,699,142 in the name of Lee et al.), but without progressive variations in step height.

FIG. 6B is a graphical representation of the diffractive profile 71 of lens 70, plotting the height of lens 70 at a particular point of echelette 72 versus ρ, the square of the radius or distance displaced from the optical axis, and shown with conventional diffractive profile 75, shown by the dotted line. FIG. 7A-7D show graphs of the diffractive profiles of individual echelettes and the diffractive efficiency in the far focus order. Optical zone 77 and transition zone 76 of each echelette 71 can be defined by Equation 1 but each using a different set of parameters. FIGS. 7A, 7B, 7C and 7D show the diffractive profiles of an echelettes having a diffractive efficiency of approximately 50%, 56%, 65% and 80%, respectively, in the far focus. Table 3A below shows a number of echelettes 71 each having a different diffractive efficiency depending on the parameters used for Function 1. Table 3B shows the parameters used and the resulting diffraction efficiency for the far focus as well as the percentage of light energy lost to higher order, non-viewing foci. The diffraction efficiencies were calculated using MATHCAD, available from Parametric Technology Corporation of Needham, Mass.

TABLE 3A

| | Focus Order | | | | | | |
|---|---|---|---|---|---|---|---|
| Echelette | −3 | −2 | −1 | 0 | 1 | 2 | 3 |
| 1 | 1.0% | 2.3% | 7.9% | 40.2% | 40.2% | 2.0% | 1.1% |
| 2 | 1.0% | 2.3% | 7.8% | 41.6% | 39.0% | 2.1% | 1.1% |
| 3 | 1.0% | 2.2% | 7.8% | 43.0% | 37.8% | 2.2% | 1.1% |
| 4 | 1.0% | 2.1% | 7.4% | 44.0% | 36.9% | 2.3% | 1.1% |
| 5 | 0.9% | 2.1% | 7.1% | 45.4% | 35.7% | 2.4% | 1.1% |
| 6 | 0.9% | 2.0% | 6.9% | 46.6% | 34.6% | 2.6% | 1.2% |
| 7 | 0.9% | 1.9% | 6.5% | 48.0% | 33.4% | 2.8% | 1.2% |
| 8 | 0.9% | 1.9% | 6.1% | 49.4% | 32.2% | 3.1% | 1.2% |
| 9 | 0.9% | 1.9% | 5.6% | 50.8% | 31.0% | 3.4% | 1.2% |
| 10 | 0.9% | 1.9% | 5.2% | 52.0% | 29.9% | 3.6% | 1.3% |
| 11 | 0.9% | 1.8% | 4.8% | 53.4% | 28.7% | 3.8% | 1.3% |
| 12 | 0.9% | 1.6% | 4.1% | 56.5% | 25.9% | 4.2% | 1.5% |
| 13 | 0.8% | 1.4% | 3.4% | 60.2% | 22.6% | 4.5% | 1.7% |
| 14 | 0.8% | 1.1% | 2.9% | 63.4% | 19.7% | 4.6% | 2.0% |
| 15 | 0.7% | 0.8% | 2.7% | 66.8% | 16.6% | 4.3% | 2.2% |
| 32 | 0.7% | 0.8% | 2.7% | 66.8% | 16.6% | 4.3% | 2.2% |

TABLE 3B

| Echelette | α | en | $r_1/q_1$ | m | Y_min | % Far | Loss |
|---|---|---|---|---|---|---|---|
| 1 | 0.4075 | 0 | 0.9999 | 10 | 0.0000001 | 50% | 20% |
| 2 | 0.4075 | 0.09 | 0.9999 | 10 | 0.0000001 | 51.6% | 19% |
| 3 | 0.4075 | 0.2 | 0.9999 | 10 | 0.0000001 | 53.2% | 19% |
| 4 | 0.4075 | 0.3 | 0.9999 | 10 | 0.0000001 | 54.4% | 19% |
| 5 | 0.4075 | 0.46 | 0.9999 | 10 | 0.0000001 | 56.0% | 19% |
| 6 | 0.4075 | 0.63 | 0.9999 | 10 | 0.0000001 | 57.4% | 19% |
| 7 | 0.4075 | 0.9 | 0.9999 | 10 | 0.0000001 | 58.9% | 19% |
| 8 | 0.4075 | 1.3 | 0.9999 | 10 | 0.0000001 | 60.5% | 18% |
| 9 | 0.4075 | 2 | 0.9999 | 10 | 0.0000001 | 62.1% | 18% |
| 10 | 0.4075 | 3 | 0.9999 | 10 | 0.0000001 | 63.5% | 18% |
| 11 | 0.4075 | 5 | 0.9999 | 10 | 0.0000001 | 65.0% | 18% |
| 12 | 0.4075 | 5 | 0.9999 | 10 | 0.000003 | 68.5% | 18% |
| 13 | 0.4075 | 5 | 0.9999 | 10 | 0.000006 | 72.7% | 17% |
| 14 | 0.4075 | 5 | 0.9999 | 10 | 0.0000036 | 76.3% | 17% |
| 15 | 0.4075 | 5 | 0.9999 | 10 | 0.0000118 | 80% | 17% |
| 32 | 0.4075 | 5 | 0.9999 | 10 | 0.0000118 | 80% | 17% |

As seen from Tables 3A and 3B, by gradually varying the shape of each echelette as a function of distance or radius from the optical axis, the diffraction efficiency for the $0^{th}$ order or far focus is gradually increased from 50% to 80%.

Experiment A

Figure 8A:
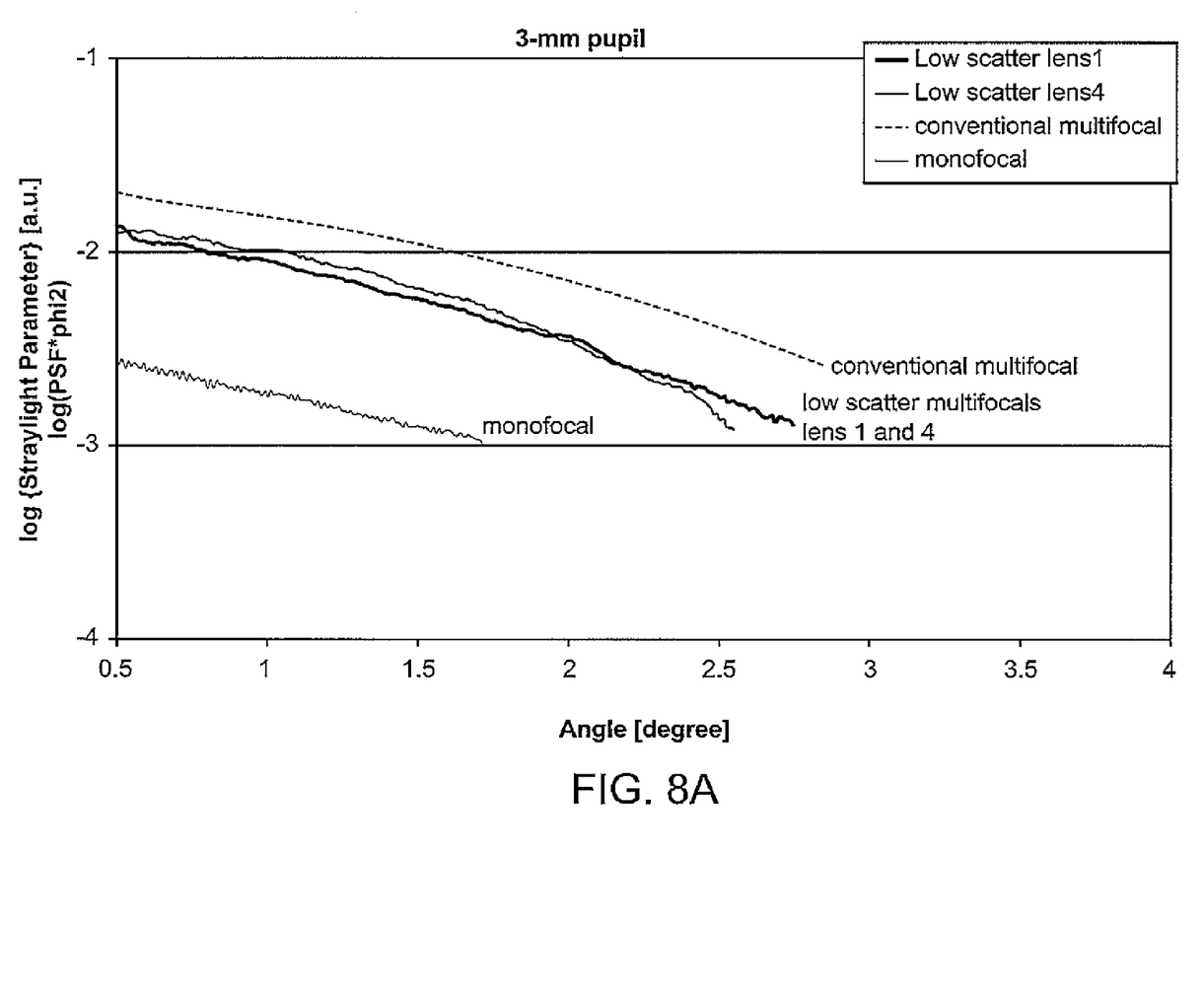
FIG. 8A-8B show graphs of the light scattering characteristics of lenses of the present invention versus other multifocal and monofocal lenses.

The light scatter characteristics of two sample multifocal lenses according to the present invention were measured and compared to that of a comparable monofocal lens and a comparable multifocal lens with a conventional diffractive profile. The conventional monofocal and multifocal lenses are generally similar except that the conventional monofocal lens has a continuous surface without a diffraction profile and a lower surface roughness. Apart from new diffractive profiles defined by a single, continuous function as previously described, the two sample multifocal lenses are identical to the conventional lenses. For instance, the sample lenses and the conventional monofocal and multifocal lenses have the same light distribution (50%:50%) between the far and near foci. The amount of scatter was measured for each of the lenses using an eye model and a bright white light source, resulting in the graph shown in FIG. 8A. The vertical axis in FIGS. 8A and 8B tracks the straylight parameter, which represents the amount of scatter. The straylight parameter is given in a logarithmic scale and is defined in the reference, van den Berg, T. J., 1995, *Optom. Vis. Sci.*, 72(2), 52-9, which is herein incorporated in its entirety. The light scatter test reveals a lower amount of light scatter from the two exemplary multifocal lenses.

Figure 8B:
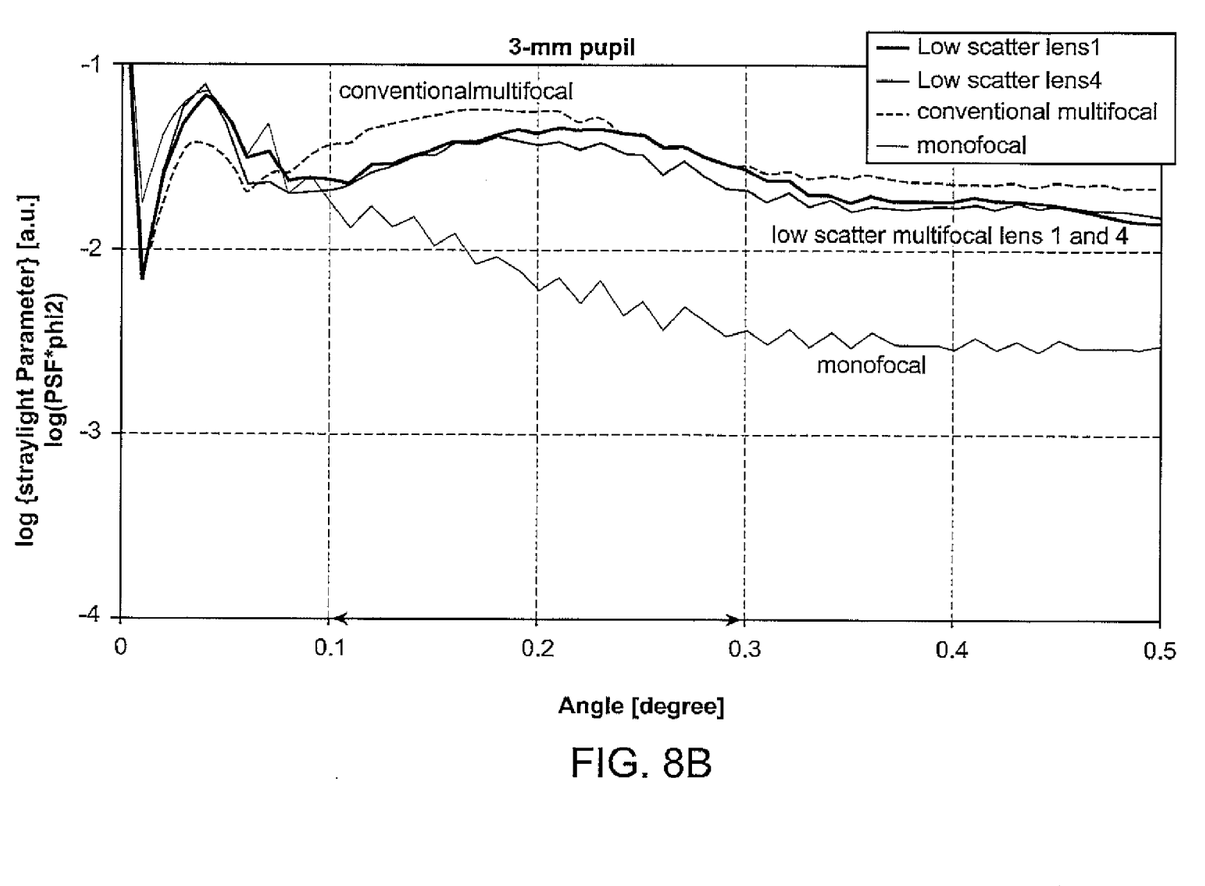

As shown in FIG. 8B, the tests also revealed a lower intensity of the primary halo. The straylight up to 0.3 degrees is attributed to the primary halo, which originates from the $1^{st}$ and $-1^{st}$ order foci. The intensity in the area of 0.1 to 0.3 degrees of the two exemplary multifocal lenses was slightly lower than that of the conventional multifocal lens.

The embodiments described above, including accompanying drawings, figures, functions and tables, are for illustrative purposes to explain aspects of the present invention. Those skilled in the art will recognize that changes and modifications can be made without departing from the scope of the invention, which is solely limited by the claims as follows.

What is claimed is:

1. A multifocal ophthalmic lens, comprising:
   an anterior face with an anterior refractive profile and a posterior face with a posterior refractive profile, the faces disposed about an optical axis;
   a diffractive profile imposed on one of the refractive profiles, the diffractive profile comprising a plurality of echelettes with associated step heights that are substantially equal to one another, the diffractive profile characterized by a continuous function over the plurality of echelettes wherein the radii of curvature of transition zones are larger than the wavelength of incoming light in order to reduce light scatter, and the diffractive profile having, in the visible waveband, a first diffractive order and a second diffractive order having a diffraction add power;
   the first and second diffraction orders having diffraction efficiencies which change with radius from the optical axis.

2. The multifocal ophthalmic lens of claim 1, wherein the anterior face and the posterior face define a clear aperture.

3. The multifocal ophthalmic lens of claim 1, wherein the echelettes comprise a central echelette and N additional echelettes, the N additional echelettes comprising a first echelette disposed about the central echelette, a second echelette disposed about the first echelette, up to an Nth echelette disposed about an (N−1)th echelette.

4. The multifocal ophthalmic lens of claim 3, wherein the first and second diffraction orders having diffraction efficiencies which change with the number of surrounding echelettes.

5. The multifocal ophthalmic lens of claim 3, wherein N is at least 4 and the first and second diffraction orders having diffraction efficiencies which change depending on the number of surrounding echelettes.

6. The multifocal ophthalmic lens of claim 1, wherein any one of the step heights does not vary by more than 20 percent from an average of all the step heights.

7. The multifocal ophthalmic lens of claim 1, wherein the diffraction efficiency of the zeroth diffractive order increases with increasing radius from the optical axis.

8. A method for viewing with a diffractive ophthalmic lens using an eye of a patient, the ophthalmic lens comprising a plurality of echelettes with associated step heights that are substantially equal to one another, the echelettes each having a characteristic profile and defining a diffractive surface, the diffractive surface characterized by smooth, continuously curving transition zones between optical zones of adjacent echelettes wherein the radii of curvature of the transition zones are larger than the wavelength of incoming light in order to reduce light scatter, and the diffractive profile having, in the visible waveband, a first diffractive order and a second diffractive order, the method comprising changing the diffractive efficiency of the second diffractive order of the echelettes with radius from the optical axis.

9. The method of claim 8, wherein changing the diffractive efficiency of the second diffractive order of each of the echelettes with radius from the optical axis comprises changing the profile of each of the echelettes with radius from the optical axis.

10. The method of claim 8, wherein the echelettes comprise a central echelette and N additional echelettes, the N additional echelettes comprising a first echelette disposed about the central echelette, a second echelette disposed about the first echelette, up to an Nth echelette disposed about an (N−1)th echelette.

11. The method of claim 8, wherein the first and second diffraction orders having diffraction efficiencies which change with the number of surrounding echelettes.

12. The method of claim 8, wherein N is at least 4 and the first and second diffraction orders having diffraction efficiencies which change depending on the number of surrounding echelettes.

13. The method of claim 8, wherein any on of the step heights does not vary by more than 20 percent from an average of all the step heights.

* * * * *